(12) United States Patent
Beers

(10) Patent No.: US 11,641,886 B2
(45) Date of Patent: May 9, 2023

(54) SANITARY PROTECTIVE PANELS

(71) Applicant: Carly Jane Beers, Canyon Lake, TX (US)

(72) Inventor: Carly Jane Beers, Canyon Lake, TX (US)

(*) Notice: Subject to any disclaimer, the term of this patent is extended or adjusted under 35 U.S.C. 154(b) by 582 days.

(21) Appl. No.: 16/686,501

(22) Filed: Nov. 18, 2019

(65) Prior Publication Data
US 2021/0145078 A1    May 20, 2021

(51) Int. Cl.
*A41B 9/04* (2006.01)
*A61F 13/82* (2006.01)
*A61F 13/551* (2006.01)
*A61F 13/15* (2006.01)

(52) U.S. Cl.
CPC ............. *A41B 9/04* (2013.01); *A61F 13/82* (2013.01); *A41B 2400/52* (2013.01); *A61F 2013/15048* (2013.01); *A61F 2013/16* (2013.01); *A61F 2013/55195* (2013.01)

(58) Field of Classification Search
CPC ............. A61F 13/47236; A61F 13/82; A61F 13/15804; A61F 13/472; A61F 13/53; A61F 13/551; A61F 13/5605; A61F 2013/15048; A61F 2013/16; A61F 2013/530029; A61F 2013/530036; A61F 2013/53035; A61F 2013/530364; A61F 2013/55195; A41B 2400/52; A41B 9/04
See application file for complete search history.

(56) References Cited

U.S. PATENT DOCUMENTS

2009/0204090 A1* 8/2009 Dennis ................ A61F 13/58 604/385.02
2019/0314210 A1* 10/2019 Sosa Guerra ....... A61F 13/5611

\* cited by examiner

*Primary Examiner* — Arti Singh-Pandey
(74) *Attorney, Agent, or Firm* — Donald R. Boys; Central Coast Patent Agency LLC

(57) ABSTRACT

A protective panel has an upper oval portion having a maximum width of between three and five inches inclusive and a vertical dimension between two and four inches inclusive, a second portion, contiguous with the first portion, extending downward from the first portion, with a gradually declining width over a vertical dimension of between eight and twelve inches inclusive, and a third lowermost portion having a width between one-half inch and two inches inclusive, ending in a circular arc at the lowermost extent, the panel formed of a polymer film having a human skin-compatible adhesive on one surface, enabling a user to apply the panel to the user's anatomy.

7 Claims, 12 Drawing Sheets

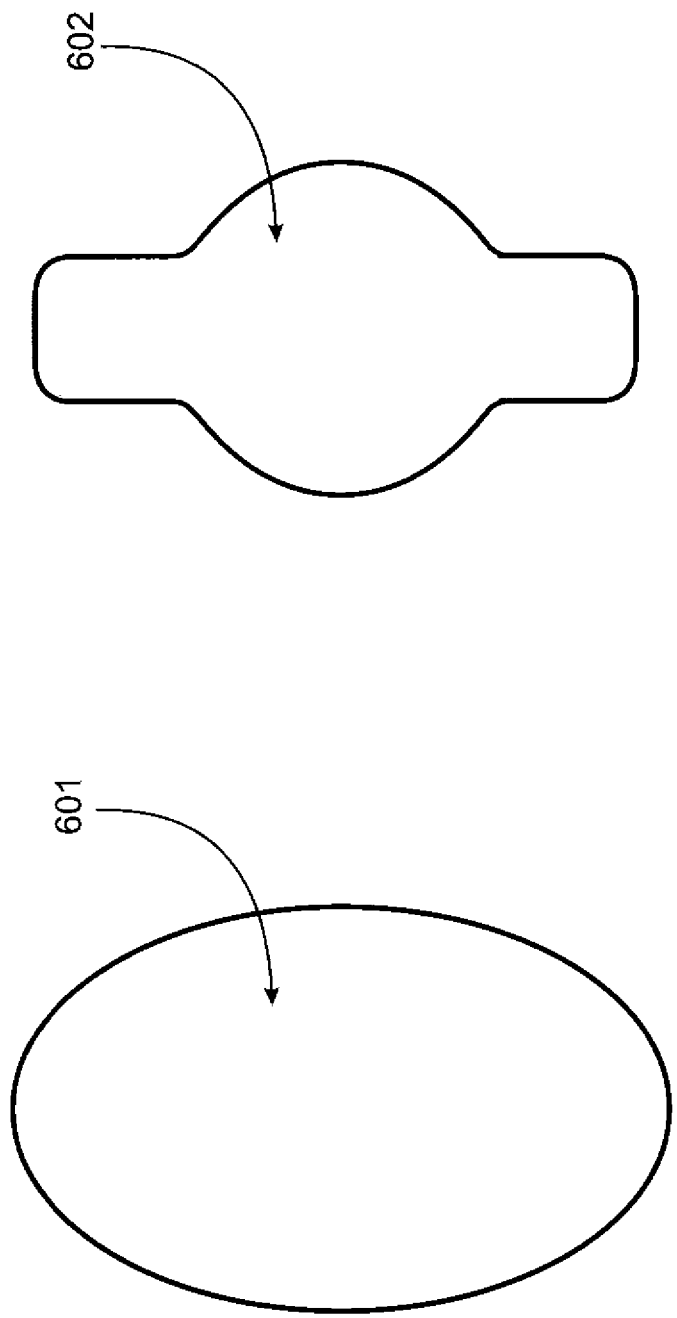

SANITARY PROTECTIVE PANELS

BACKGROUND OF THE INVENTION

1. Field of the Invention

The present invention is in the technical area of sanitary protection regarding human genitalia and pertains more particularly to provision of protective panels for use to shield a person's genitalia under various circumstances.

2. Description of Related Art

In retail transactions involving items of clothing it is well-known that customers of a retail establishment are motivated to try on articles of interest before agreeing to purchase, and most retail outlets have changing rooms with mirrors and clothes hangers where customers may take articles of clothing to try on same, and observe the fit and appearance in the selected clothing.

A very serious drawback in such retail outlets is simply that many, if not most customers, especially in enterprises offering such as lingerie, for example, are reluctant to try on articles that other customers may have already tried on. The problem being one of sanitation, and fear of contamination. It is well known, for example, that many diseases may be transmitted from bacteria or viruses that may be trapped on articles that have come into contact with genitalia.

It is known in the art that some retail establishments may have clothing for try-on that have protective panels sewn into the genital or underarm regions of the clothing. This may be seen as protecting the clothing but does nothing for protecting customers from cross-contamination.

What is clearly need is a dispensary of sanitized protective panels that persons, such as customers at a retail establishment, may remove from a sanitary enclosure, apply to the person's own genital or underarm areas, or both, and discard when no longer needed, such as by disposal in a closed container.

BRIEF SUMMARY OF THE INVENTION

In one embodiment protective panel is provided, comprising a first upper portion having a substantially oval shape, of an areal extent sufficient to cover a pubic mound of a female anatomy, the first portion having a maximum width of between three and five inches inclusive and a vertical dimension between two and four inches inclusive, a second portion, contiguous with the first portion, extending downward from the first portion, with a gradually declining width over a vertical dimension of between eight and twelve inches inclusive, and a third lowermost portion having a width between one-half inch and two inches inclusive, ending in a circular arc at the lowermost extent. The panel is formed of a polymer film having a human skin-compatible adhesive applied to one surface, enabling a user to apply the panel with the first portion covering the pubic mound with the adhesive on the one surface adhering the user's skin around the top and sides of the pubic mound, the second portion extending between the user's legs, covering a vaginal opening and an anal opening of the user's anatomy, with the third portion extending to a point on or above the user's buttocks, the adhesive on the one surface adhering to the user's skin on or above the user's buttocks.

In one embodiment the material of the polymer film is waterproof and impermeable. Also, in one embodiment the adhesive is applied evenly over all of the one surface of the protective panel. In one embodiment the protective panel is sanitary at time of application.

In another aspect of the invention a sanitary panel system is provided, comprising a sanitized protective panel comprising a thin sheet of impermeable material having a wide region at one end for covering a pubic mound of a female torso, the wide region tapered over a length of from eight to twelve inches as an elongated, more-narrow region, ending in a rounded end at least one inch in width, the elongated region for passing between the legs and up between and over the buttocks, the panel having a front side, and a back side comprising an adhesive for adhering the panel to skin of a user, and a substantially rectangular pocket formed by two sheets of sterile polymer film, one sheet of which is transparent, the two sheets heat sealed along all four edges, enclosing the protective panel. The sanitized protective panel with the adhesive is enclosed in the substantially rectangular pocket.

In one embodiment of the system both sheets of sterile polymer film are transparent. Also, in one embodiment the seal along one edge of the substantially rectangular pocket has a nick through most of the width, enabling a user to open the pocket and remove the sanitary protective panel for use.

In another aspect of the invention a method for providing sanitary protective panels for personal use is provided, comprising sequentially cutting panels from a continuous strip of impermeable polymer film, applying adhesive to one side of the panels, sanitizing the panels, placing the panels sequentially on an advancing sterile film, covering the panels by a second advancing sterile film, heat sealing opposite sides of the advancing sterile films together, heat sealing across the advancing films between each panel enclosed between the films, creating heat sealed cross strips creating individual pockets each enclosing one panel, perforating a line centered on the heat sealed cross strips, and rolling the sealed films into a finished roll for storage.

In one embodiment the method further comprises cutting a nick though a portion of width of one heat sealed side of the sealed films, one nick along a side of each heat sealed pocket. Also, in one embodiment the method comprises placing a roll of individual pockets holding sanitary panels into a dispenser, with one end of the roll extending outside the dispenser through an opening, enabling a user to grasp one pocket, and to tear off that pocket along the perforated line between that pocket and the next pocket in the roll. In another embodiment the method further comprises a step of the user opening the pocket torn off at the perforated line at the nick along one side, and removing the enclosed sanitary panel. And in one embodiment the method further comprises separating individual ones of the pockets at the perforated lines, organizing the separated pockets into a discrete stack, and placing the stack of pockets into a box with an open top, enabling a user to remove one pocket at a time for use.

In yet another aspect of this invention a method for safely trying on articles of clothing at a retail outlet is provided, comprising steps of acquiring a pocket comprising two opposing films enclosing an elongated sanitary protective panel having a wide region at one end for covering a pubic mound of a female anatomy, the wide region tapered to an elongated, more-narrow region, the elongated region for passing between the legs and up between and over the buttocks, the panel having a front side, and a back side treated with an adhesive for adhering the panel to skin of a user, the opposing films heat sealed around the edges forming the pocket, tearing open the pocket and removing the elongated sanitary protective panel, and before trying on the articles of clothing, placing the wide region over the pubic mound in front, with the adhesive side toward the skin, drawing the elongated more narrow region between the legs and upward between and over the buttocks, and adhering the more narrow region to the buttocks by the adhesive, protecting the vaginal and anal openings from any contaminant on an article of clothing.

In one embodiment of this method the pocket is an end pocket in a roll of joined pockets having a perforated strip between pockets, in a roll in a dispenser with an opening for providing an end pocket of the roll outside the dispenser. And in one embodiment the pocket is one of a plurality of separate pockets in a stack in a dispenser box with an open top, wherein a user may remove pockets one-by-one.

BRIEF DESCRIPTION OF THE SEVERAL VIEWS OF THE DRAWINGS

FIGS. 6A and 6B depict more alternative shapes of protective panels in another embodiment of the invention.

DETAILED DESCRIPTION OF THE INVENTION

Figure 1:
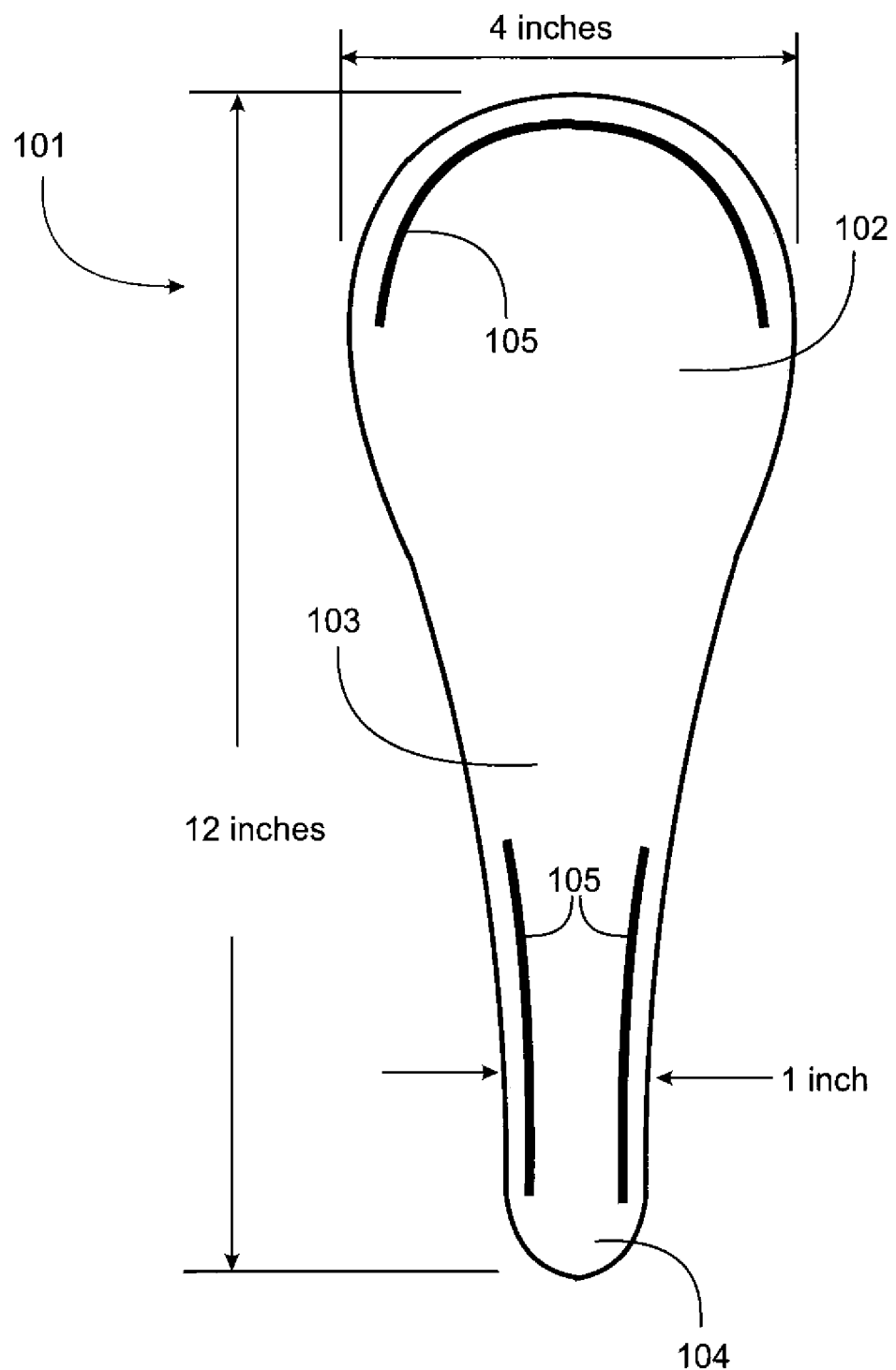
FIG. 1 is a plan view of a sanitary protective panel in an embodiment of the present invention.

FIG. 1 is a plan view of a sanitary protective panel 101 in an embodiment of the present invention. Panel 101 is a thin, shaped panel of polymer material, for example certain varieties of surgical tape. It is important that the material not be porous, or open cell, as an important purpose is to prevent penetration through the panel of bacteria, virus material, or liquids or semi-liquids, such as bodily fluids. In some embodiment the material may be hermetic. There are many plastic materials that may be suitable, and for some embodiments it is preferred that the panel material be opaque.

In this example panel 101 has an upper portion 102 in a shape of an oval with a widest portion at a centerline of the oval shape. In one embodiment the width may be about four inches but may vary in different embodiments from about three to about five inches. The panel has a lower section 103 tapering in width below upper section 102 from the width of four inches to a lower width of one inch at the lowermost rounded region Lines 105 of adhesive are placed on the panel in strategic peripheral places as shown. In some cases, the adhesive may as spots rather than lines. Spots may be oblong or oval.

Figure 2A:
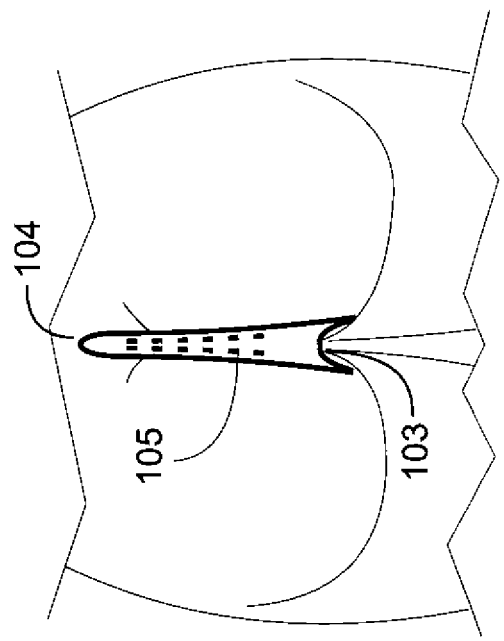
FIG. 2A is a front elevation view of a midsection of a female person using a sanitary protective panel in an embodiment of the invention.
Figure 2B:
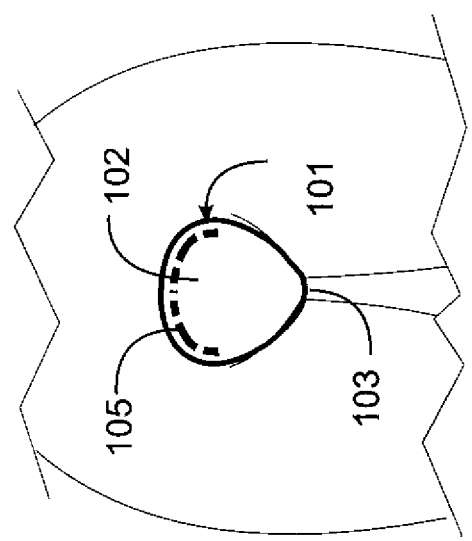
FIG. 2B is a rear elevation view of the midsection of the female person of FIG. 2A using a sanitary protective panel in an embodiment of the invention.

FIGS. 2A and 2B illustrate a use of sanitary protective panel 101 in an embodiment of the invention. In FIG. 2A the essential shape of a female midsection is shown from a front view, outlined in relatively light lines, and in FIG. 2B the female midsection is illustrated from a back view, also in relatively light lines. Referring again to FIG. 2A, sanitary protective panel 101 is illustrated as mounted to the female form with the four-inch width of portion 102 positioned above the mons pubis (aka pubic mound), and the length of portion 102 descending to cover the front of the genital region, and to reach between the legs.

In this example panel 101 is joined to the female body by adhesive lines 105 around the periphery of section 102. When the user mounts panel 101, lower portion 103 will be suspended down the front of the user. This portion is passed between the legs and pulled up between the buttocks. In FIG. 2A this step has already been accomplished.

In back view FIG. 2B, the lower end 104 of panel 101 at one inch wide is shown as mounted to the lower back of the female form above the buttocks, by one or more adhesive spots or lines of adhesive. Thus mounted to the female form, section 103 passing between the legs covers and protects both the vaginal opening and the anal opening, such that bacteria and fluids encountered in any activity may not enter these openings, and conversely, no fluid, material or such as bacteria from the wearers genital openings may be spread to any adjacent clothing or other person in any activity.

The inventor believes there are a variety of use cases for a sanitary protective panel according to embodiments of the present invention. One such is as pointed out in the background section above, that of retail clothing outlets where customers wish to try on articles of clothing but may hesitate because of the grossly unsanitary circumstance of putting on an article of clothing that another has worn next to the genitalia. Dispensing systems for sanitary protection panels according to the invention are described in enabling detail below, and a dispensing system may be provided in or near changing rooms in such retail outlets. Customers are enabled to take a sanitary protection panel from an enclosure, to don the panel, and to wear the panel while trying on different articles of clothing and are enabled to dispose of the panel in a sanitary manner after use. This practice protects both the customer and the business.

Another use case is in the practice of therapeutic massage, where clients may use such panels to avoid being completely exposed during massage sessions. The panels may also be fashioned for male use, wherein the upper panel may be somewhat wider or higher, and the male genitalia may be covered by the way the panel is positioned to the user's anatomy. Transgender individuals may find panels according to embodiments of the invention useful for hiding or taping back genital extremities.

There are many potential usages in medical practice, where patients may wish to cover the genitalia during an examination, for example. Such panels may be used when taking photos in medical examinations and diagnoses. The panels are also useful in any circumstance where a person needs to remove clothing to a near naked state but not completely naked. Sanitary disposal for medically related panels may have more emphasis than others. For example, a package that the panel comes in may also be used for disposal. The panels may be used for tanning beds so genitals are not exposed to ultraviolet (UV) radiation while tanning. In this use case the material may be UV resistant.

Persons may use such panels to protect the genital area from sand at the beach while still allowing for bikini exposure. The panels may also useful for such as mud runs, and any other activity where sealing the vaginal and anal openings from exposed elements is desired. The panels may be used by actors in shooting sex scenes where near full nudity may be required while still protecting and covering genitals of male and female from both physical and visual contact. Ladies that want to avoid panty line may use the panels instead of panties. With perhaps a shield lining, such as lead, panels according to the invention may protect pilots and scientists from harmful radiation.

Another use case derives from persons who want a sanitary alternative to conventional underwear. It is well known that excreta from the two genital openings, whether male or female, almost always stain and contaminate male and female panties and shorts. And it is not just the unsightly stains that are difficult for the laundry system to erase that is the problem. These stains are basically unsanitary, and bacteria and viruses can cross-contaminate other clothing and persons. Many persons may well choose to use a panel according to an embodiment of the invention to eliminate this unsightly and potentially dangerous circumstance. Such persons may well use one panel on dressing in the morning and carry one or panels during the day to use as needed. There may also be a sanitary disposal container for this use case.

Figure 3B:
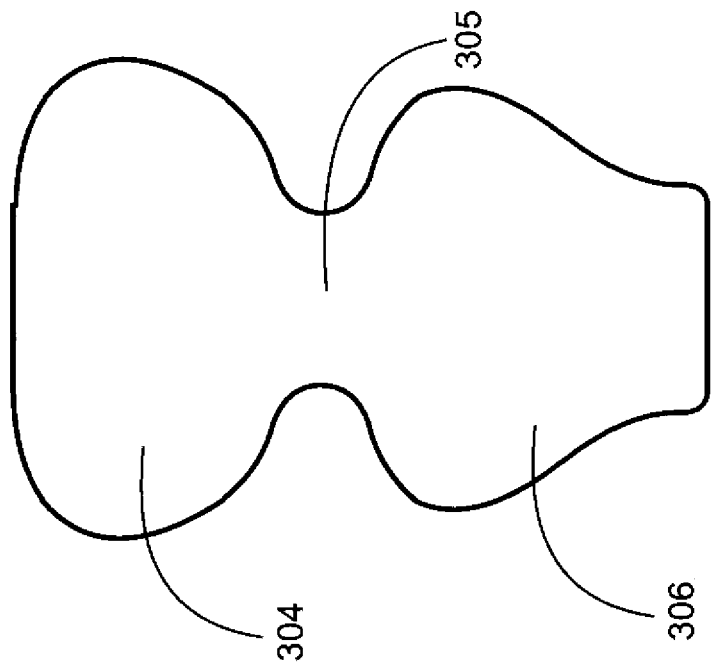
FIGS. 3A and 3B depict alternative shapes of protective panels in an embodiment of the invention.
Figure 3A:
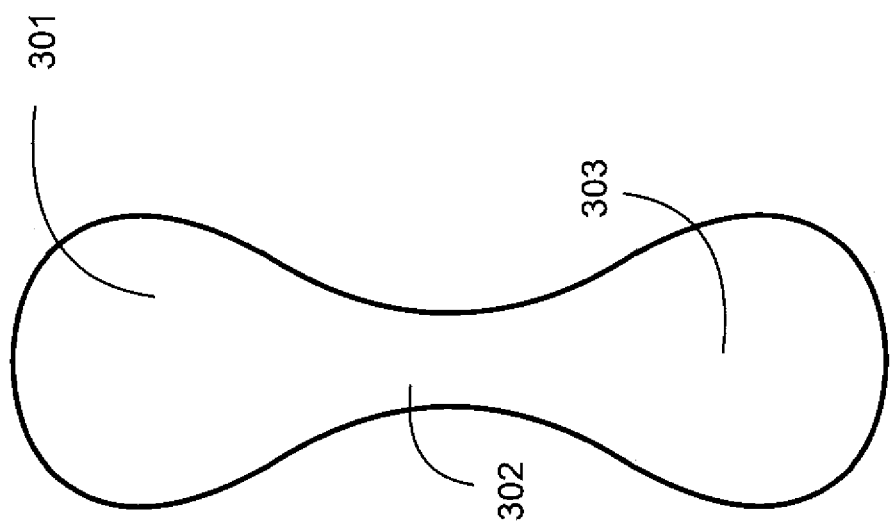

FIG. 3A is a plan view of a sanitary protective panel in an alternative embodiment of the present invention. In the panel of FIG. 3A there are two wider oval regions connected by a more narrow region. This panel may be used with either oval region at the front, and the other will make a wider shield behind the buttocks. FIG. 3B illustrates a panel intended for use by males, having wider regions.

Figure 4B:
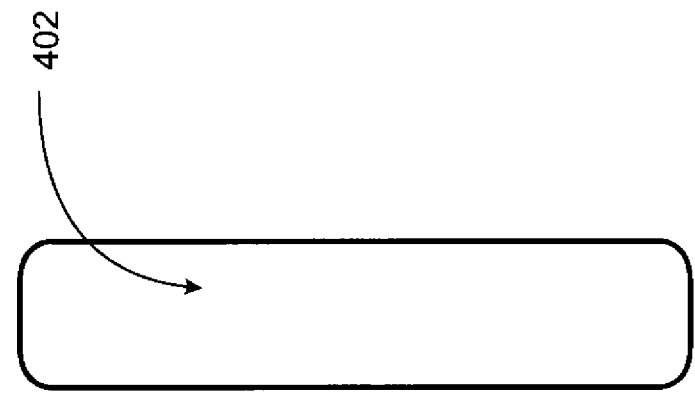
FIGS. 4A and 4B depict alternative shapes of protective panels in another embodiment of the invention.
Figure 4A:
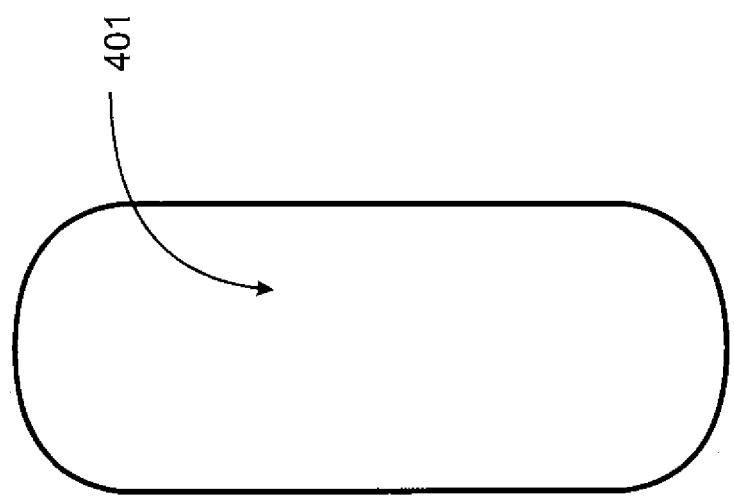
Figure 5B:
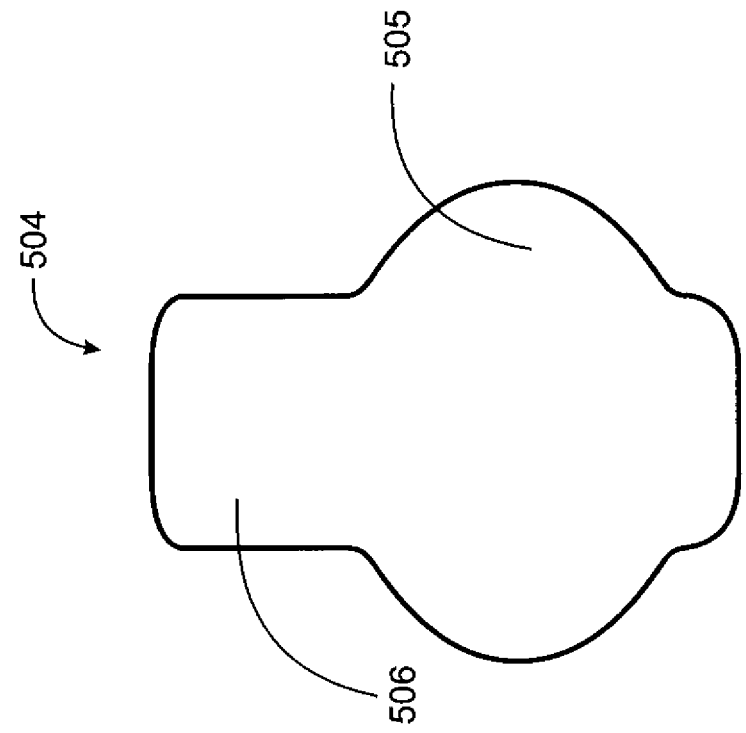
FIGS. 5A and 5B depict alternative shapes of protective panels in another embodiment of the invention.
Figure 5A:
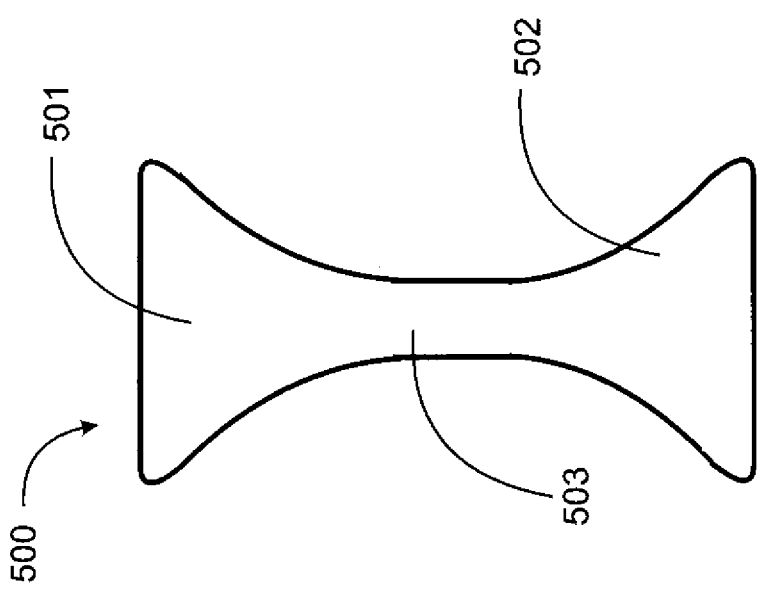

FIGS. 4A and 4B illustrate still more alternative shapes that are simpler in geometry. FIGS. 5A and 5B show more alternative shapes. FIGS. 6A and 6B illustrate shapes that might be used for underarm protection.

It has been described above that the panels in embodiments of the invention are sterile at the point in time that the user applies the panels to the user's body. This is because an important purpose is to prevent contamination for the user when, for example, trying on a garment that another person may have tried on, and that may therefore be contaminated with that other person's body fluids and bacteria, or even viruses.

Figure 7A:
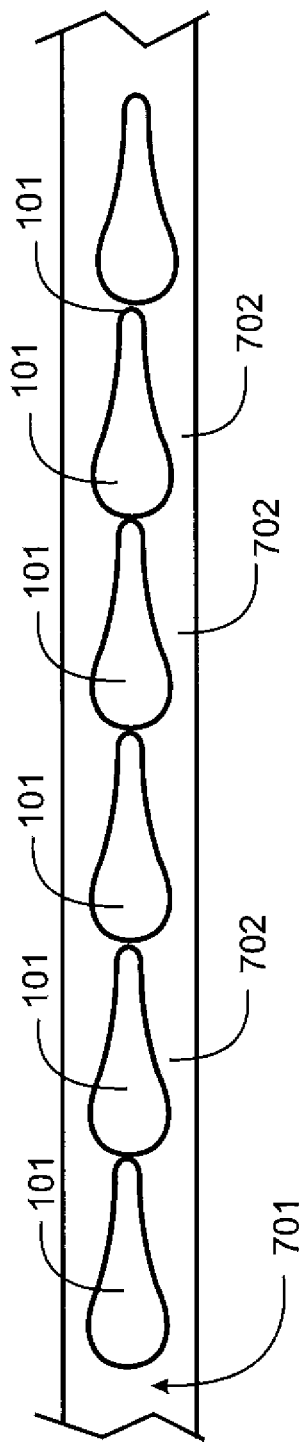
FIG. 7A shows a material strip with sanitary protective panels shown as sequential cut-outs.
Figure 7B:
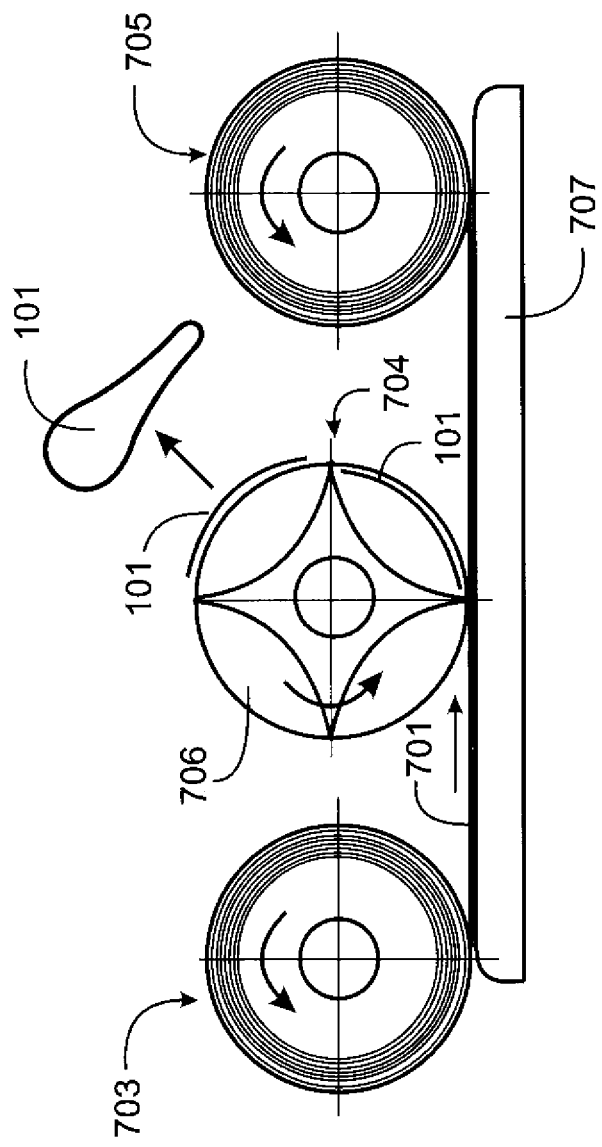
FIG. 7B is an elevation view of apparatus cutting sanitary protective panels from a continuous strip of material.

For it to be the case that the panels are always sterile at the point of use, the panels must be sterile at time of manufacture, and must be packaged and delivered in a way that the panels are sterile at the time that a user accesses a panel for personal use. FIGS. 7A and 7B are diagrams illustrating an exemplary process of manufacture.

FIG. 7A is a plan view of a strip of film 701 of a material and thickness suitable for a sanitary panel according to an embodiment of the present invention, preferably non-porous, of as thickness to be resistant to tearing or stretching. Film 701 is of a width such that cutting a panel 101 from film 701 will leave film on each side (702), enabling the film to be moved forward or backward as a whole before or after panels may be cut from the film. Panels 101 are shown end-to-end along a length of film 701.

FIG. 7B is an exemplary illustration depicting one way that panels 101 may be cut from film strip 701. In this example a substantial length of film 701 is provided on a roll 703, and film 701 is drawn along a backing panel 707 by a second roller 705, which rolls up used film after panels are cut from the film. Roller 705 may be powered and roller 703 may not be powered. A cutting roller 704 has, in this example, four cutting elements 706 that have cutting edges shaped to cut the shape of panels 101 from the advancing film. Roller 704 turns at just the necessary RPM to track along advancing film 701. As cutting elements 706 cut individual panels 201 from film 701, the panel just cut is retained on the cutting element as roller 704 turns and is removed at some point after the cutting process is complete. There are a variety of ways this may be accomplished, such as with suction cups on mechanical arms, and a variety of ways the cut panels may be collected and moved further through the process. An individual panel 101 is shown removed from a cutting element and turned arbitrarily to show the shape of the panel.

Figure 8A:
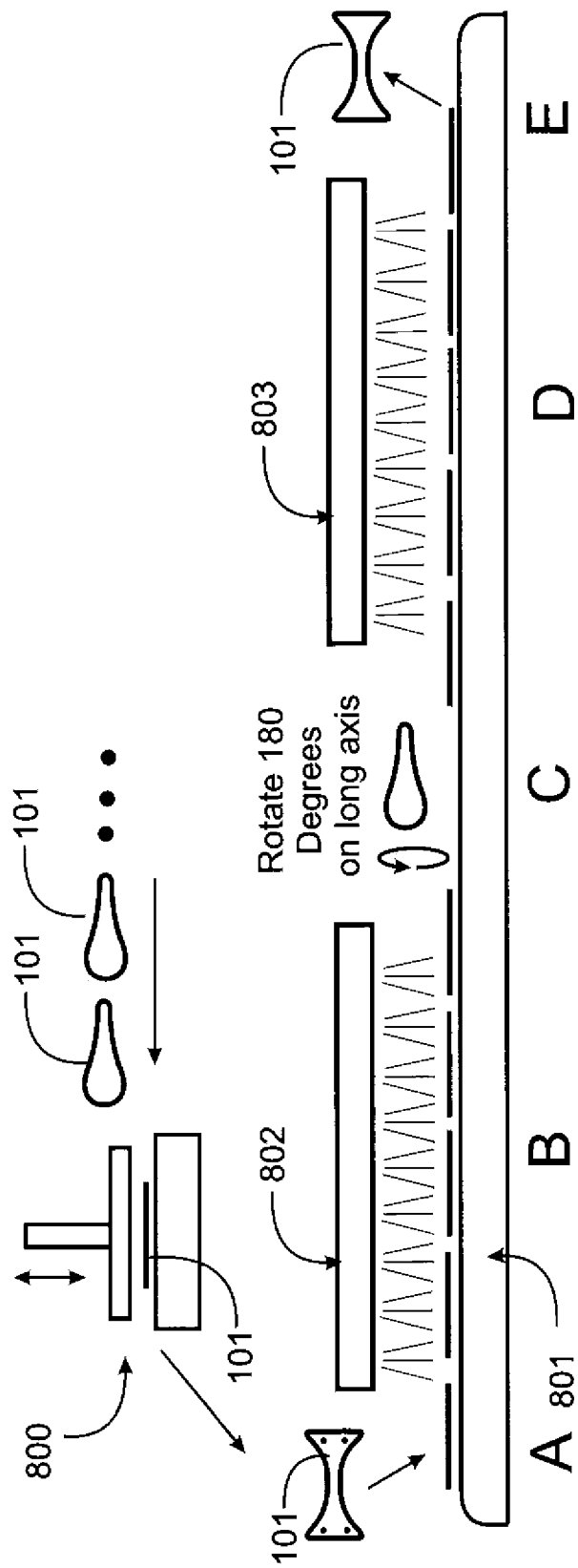
FIG. 8A shows apparatus applying adhesive to sanitary protective panels and sanitizing panels on both sides.

At the time of removal from the cutting elements the individual panels are formed, but not provided with adhesive, or cleaned or sanitized. FIG. 8A illustrates individual panels 101 being placed on an adhesive placement apparatus 800, where adhesive is added to each panel, after which panels with adhesive added are placed one at a time at a point A and translated along a path conveyance 801 through a region B where one side of each panel is cleaned and sanitized by a sanitizing apparatus 802. At point C along conveyance 801 panels 101 are rotated one hundred and eighty degrees around the length of the panel and placed back on conveyance 801. The panels then pass through a region D where the opposite side of each panel is cleaned and sanitized using a second sanitizing apparatus 803. At point E the panels are removed from the conveyance using sanitary apparatus and moved to another step in the process, keeping the panels sanitary in the process.

Figure 8B:
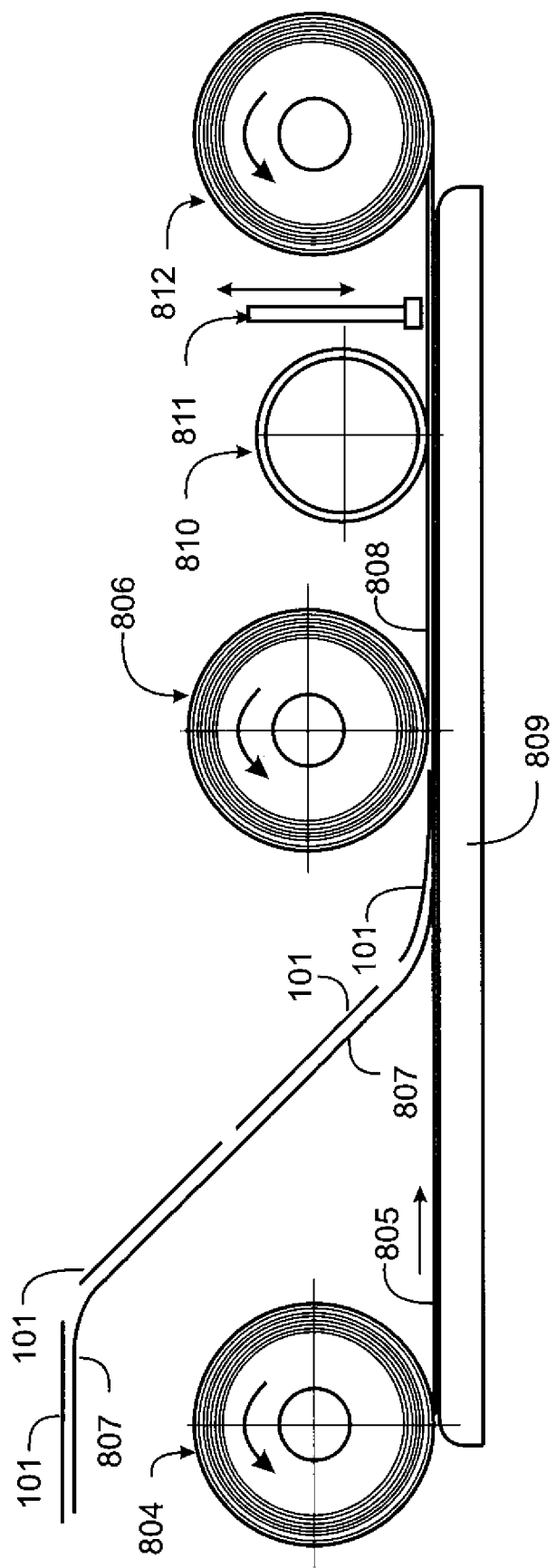
FIG. 8B is an elevation view of apparatus placing and capturing sanitary protective panels between two strips of film.

FIG. 8B is an elevation view of an exemplary apparatus packaging individual panels 101 between transparent sanitary plastic films, and heat sealing the films to enclose and protect the panels 101. In the example of FIG. 8B a roller 804 has a rolled length of transparent heat sealable film 805 of a width somewhat wider than the width of panels 101. There are several candidates for such film, such as, for example, polyethylene, polyolefin, polypropylene, and others. Film 805 is drawn along a backing panel 809 by a powered roller 812. Sanitary panels 101 are brought along a conveyance 807 and placed on film 805 as that film passes a point where the panels are placed. A roller 806 feeds a second transparent film 808 from a roller 806 over the top of panels 101 on film 805, sandwiching panels 101 between films 805 and 808. As the films advance further, with panels 101 captured between the films, a heat-sealing roller 810 seals opposite edges of films 805 and 808 together, and advancing further, a heat sealing bar 811 heat seals a strip 815 (see FIG. 8C) and also perforates a line in the center of the heat seal strip between each panel, enabling individual enclosed sanitary panels to be separated from the heat sealed strip. Dimension "s" (see FIG. 8C) represent the distance between panels 101 in the heat-sealed strip. The joined films enclosing panels 101 are rolled up finally on roller 812.

Figure 8C:
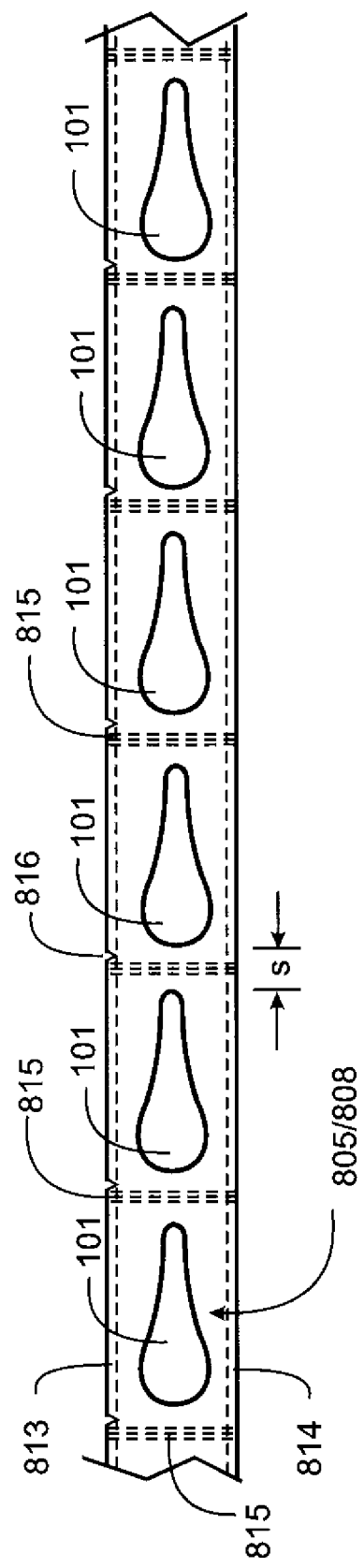
FIG. 8C is a plan view of sanitary protective panels captured between film strips with heat sealed edges and cross seals.

FIG. 8C illustrates the heat-sealed films 805 and 808 with panels 101 enclosed in individual pockets, formed by heat-sealed regions 813 and 814 along each side, and heat-sealed regions 815 between each panel 101. Regions 815 also have a perforated line for tearing off panels 701 from the strip.

Figure 9A:
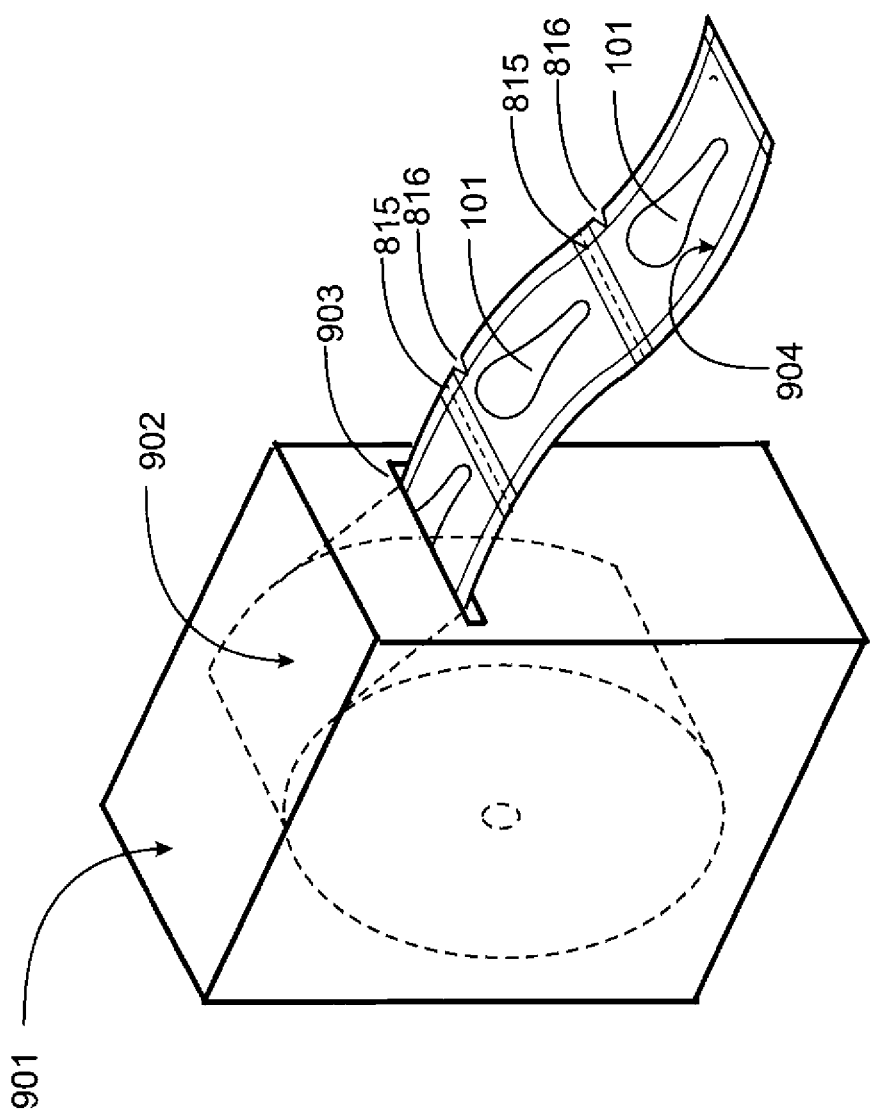
FIG. 9A is a perspective view of a dispenser providing packed sanitary protective panels in a strip for tearing off.

FIG. 9A illustrates a dispenser 901 enclosing a rolled inventory 902 of packaged panels 904, comprising individual panels 101 enclosed in film in a continuous roll enabled to feed packages 904 through a dispensing opening 903. Dispenser 901 may be mounted in a dressing room in a retail establishment, or in a central location in the retail establishment, and customers may tear off packages 904 one-by-one for personal use, along perf lines 815. The customer, having torn off one packaged panel, may tear open the sealed double film at a nick 816 on one side provided for the purpose (see also FIG. 8C for nick 816), to access a sanitary panel 101 with adhesive in the package.

Figure 9B:
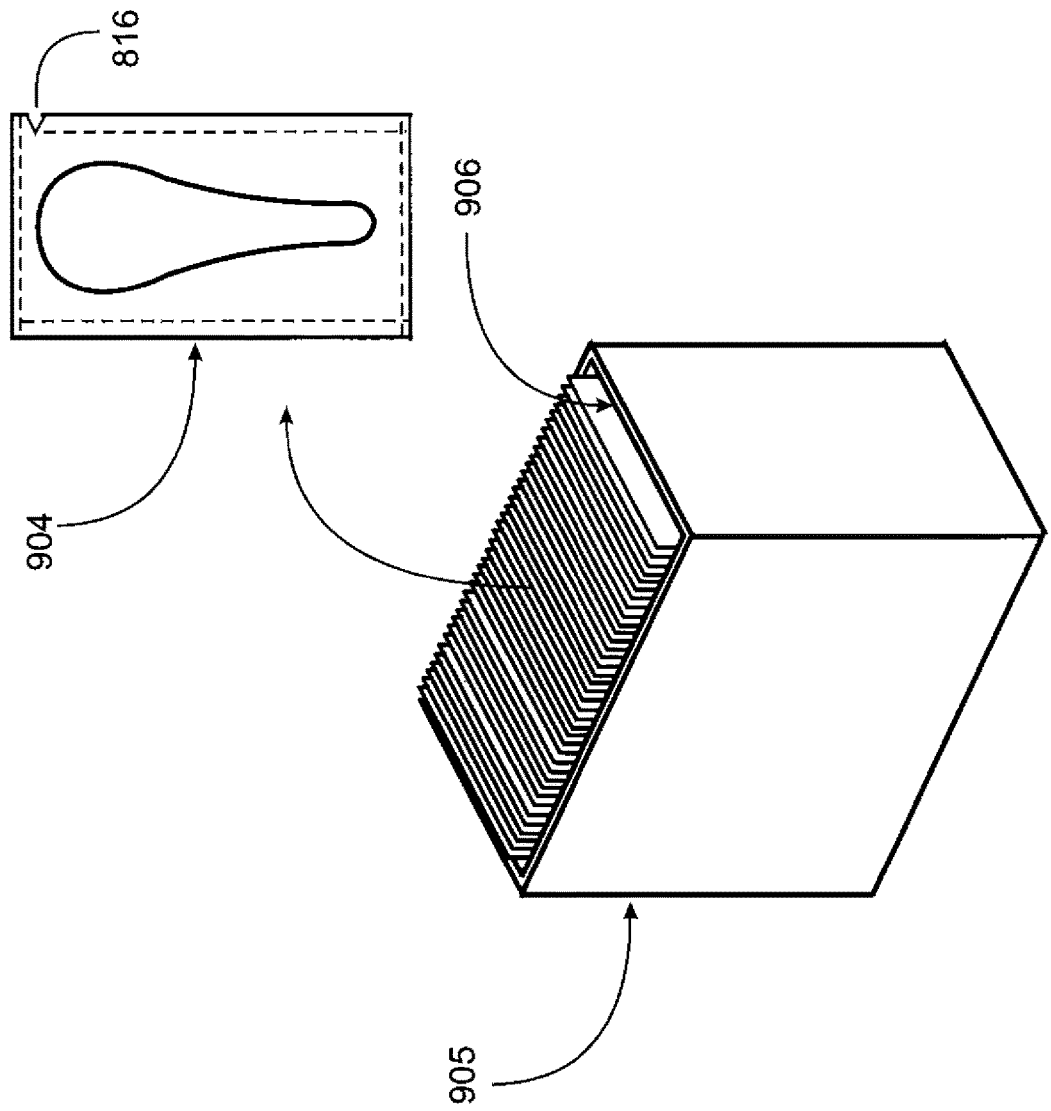
FIG. 9B is a perspective view of individual packages holding sanitary protective panels in a dispenser box for a user to take one-at-a-time.

FIG. 9B illustrates a dispenser box 905 having an open top 906, in which individual units 904, being each one an enclosed panel from a continuous strip, are displayed for use. The individual units may be automatically cut from the continuous strip and may be packed in dispenser boxes 905 as shown in FIG. 9B. A dispenser box of this sort may be placed in or near a changing room in a retail establishment, or individual units may be packed in units of such as two, five or ten, for example, to be sold to individual consumers, to be carried in a purse or a pocket for use as needed. The dispenser box has a removable top, not shown, that is closed when the dispenser is not in use.

FIG. 9B shows one package 904 having been removed from box 905, and shows nick 816, where a user may open the package to remove the sanitary panel 101 for personal use. In some embodiments a separate compartment may be provided with box 905 where the user may discard the panel 101 after use, and the package it came in as well. In other circumstances conventional trash receptacles may be provided for disposal of used panels and packages.

The adhesive with which a user applies a sanitary protective panel to his or her person in embodiments of the invention is a very important issue. There are adhesives for this purpose known in the art, and in most embodiments a suitable adhesive is selected from known adhesives. The nature of location and extent of the adhesive on a panel in embodiments of the invention is also an important issue. In some embodiments a panel according to an embodiment of the invention may be covered completely, or nearly so, on one side of the panel. A small region at one edge may be left sans adhesive so a user may grasp that small region to remove the panel after use. In some embodiments, adhesive may be applied to a panel in a continuous line around a periphery of a panel, and in other instances adhesive may be in spots as needed.

A person of skill in the art will understand that the embodiments described above are entirely exemplary, and not limiting to the scope of the invention. There may be many changes made in the embodiments shown above within the scope of the invention.

The invention claimed is:

1. A protective panel, consisting of: a polymer film fully continuous within a peripheral shape symmetrical about a vertical axis, comprising: a first side surface fully exposed; a first upper portion having a substantially oval shape, of an areal extent sufficient to cover a pubic mound of a female anatomy, the first upper portion having a maximum width of between three and five inches inclusive and a vertical dimension between two and four inches inclusive; a second portion, contiguous with the first upper portion, extending downward from the first portion, with a gradually declining width over a vertical dimension of between eight and twelve inches inclusive; a third, lowermost portion, contiguous with the second portion, having a width between one-half inch and two inches inclusive, ending in a circular arc at the lowermost extent; and a human skin-compatible adhesive applied to a second side surface of the panel in an arcuate shape across the top of the oval shape of the first upper portion, proximate an upper edge of the upper portion, and along opposite vertical edges of the third, lowermost portion, enabling a user to apply the panel with the first upper portion covering the user's pubic mound with the adhesive on the one surface adhering to the user's skin around the top and sides of the pubic mound, the second portion extending between the user's legs, covering a vaginal opening and an anal opening of the user's anatomy, with the third portion extending to a point on or above the user's buttocks, the adhesive along opposite vertical edges of the third, lowermost portion adhering to the user's skin on or above the user's buttocks, the panel thus covering and protecting both the vaginal opening and the anal opening, such that bacteria and fluids encountered in any activity may not enter these openings, and conversely, no fluid, material or such as bacteria from the wearers genital openings may be spread to any adjacent clothing or other person in any activity.

2. The protective panel of claim 1 wherein the material of the polymer film is waterproof and impermeable.

3. The protective panel of claim 1 wherein the human skin-compatible adhesive comprise lines of adhesive, continuous or discontinuous, a first line in an arc symmetrical around the vertical axis of symmetry, following at least a part of the curved upper part of the first upper portion of the panel, and a second and a third line, continuous or discontinuous, each proximate an opposite vertical edge of the third lowermost portion of the panel.

4. The protective panel of claim 1 wherein the protective panel is sanitary at time of application.

5. A sanitary panel system, consisting of: a polymer film continuous within a peripheral shape symmetrical about a vertical axis, comprising a first upper portion having a substantially oval shape, of an areal extent sufficient to cover a pubic mound of a female anatomy, the first upper portion having a maximum width of between three and five inches inclusive and a vertical dimension between two and four inches inclusive, a second portion, contiguous with the first upper portion, extending downward from the first portion, with a gradually declining width over a vertical dimension of between eight and twelve inches inclusive, a third, lowermost portion, contiguous with the second portion, having a width between one-half inch and two inches inclusive, ending in a circular arc at the lowermost extent, and a human skin-compatible adhesive applied to one surface of the panel in an arcuate shape across the top of the oval shape of the first upper portion, proximate an upper edge of the upper portion, and along opposite vertical edges of the third, lowermost portion;

and substantially rectangular pocket formed by two sheets of sterile polymer film, one sheet of which is transparent, the two sheets heat sealed along all four edges, enclosing the protective panel.

6. The sanitary panel system of claim 5 wherein both sheets of sterile polymer film are transparent.

7. The sanitary panel system of claim 6 wherein the seal along one edge of the substantially rectangular pocket has a nick through most of the width, enabling a user to open the pocket and remove the sanitary protective panel for use.

* * * * *